United States Patent [19]
Kubo et al.

[11] Patent Number: 5,061,182
[45] Date of Patent: Oct. 29, 1991

[54] DENTURE BASE STABILIZING SHEET

[75] Inventors: Masakazu Kubo, Yokohama, Japan; Robert Berghash, Tonawanda, N.Y.

[73] Assignees: Kabushiki Kaisha Showa, Tokyo, Japan; Brimms Inc., Tonawanda, N.Y.

[21] Appl. No.: 410,139

[22] Filed: Sep. 21, 1989

[51] Int. Cl.⁵ .............................................. A61C 13/00
[52] U.S. Cl. .................................................. 433/199.1
[58] Field of Search ...................................... 433/199.1

[56] References Cited

FOREIGN PATENT DOCUMENTS

| | | |
|---|---|---|
| 49-108887 | 10/1974 | Japan . |
| 54-123695 | 2/1978 | Japan . |
| 5538172 | 9/1978 | Japan . |
| 5759529 | 9/1980 | Japan . |
| 57-206604 | 6/1981 | Japan . |
| 59-172413 | 3/1984 | Japan . |

Primary Examiner—V. Millin
Attorney, Agent, or Firm—Nixon & Vanderhye

[57] ABSTRACT

A denture base stabilizing sheet fitting the shape of the user's jaw serves to stabilize the denture base on the jaw. The sheet has a generally trapezoidal configuration, optionally with a cut out in the center, with each corner of the trapezoid having smooth edges. The sheet is made from a composition containing 41 to 43 wt % ethyl methacrylate polymer, 37 to 39 wt % butyl phthalyl butyl glycolate, and 17 to 23 wt % glyceryl triacetate.

8 Claims, 3 Drawing Sheets

DENTURE BASE STABILIZING SHEET

BACKGROUND OF THE INVENTION

This invention relates to a denture base stabilizing sheet (denture base fixing sheet) fitting the configurations of a user's jaw and a denture base, which serves to stabilize a denture base on the jaw.

Conventionally, a denture base stabilizing material made of a synthetic resin in the form of powder, paste or a soft plate has been used as the means for stabilizing a denture base on the jaw. Each time a user attaches a denture base to user's jaw, the user takes the required amount of denture base stabilizing material from a receptacle in the case of a powder or paste sheet, or forms it into an appropriate size and configuration in the case of a soft sheet, for the purpose of filling any gaps left between the denture base and user's jaw with the denture base stabilizing material.

Examples of conventional denture base stabilizing sheet of the above-mentioned soft sheet type are: a plastic material for lining denture bases, comprising polyethylene, polypropylene, polybutene, polyvinyl chloride, ethylene-vinylacetate copolymer, nylon, polyvinyl fluoride, Teflon, polyacrylonitrile and polyvinyl alcohol disclosed in Japanese Patent Laying Open (KOKAI) No. 57-59529; a thin sheet for stabilizing a full set of dentures disclosed in Japanese Utility Model Laying Open (KOKAI) No. 59-172413; a sheet for fixing dentures disclosed in Japanese Utility Model Laying Open (KOKAI) No. 54-123695; and a denture base stabilizing sheet disclosed in Japanese Utility Model Laying Open (KOKAI) No. 61-196723 which is proposed by the inventors of the present invention.

However, with the above-mentioned conventional sheet, the user is obliged, each time the user attaches a denture base to user's jaw, to perform the bothersome operation of taking the required amount of denture base stabilizing material in the form of powder or paste and disposing it on the denture base, or of forming the denture base stabilizing sheet into a soft sheet type conforming to the size and configuration of the denture base. In particular, the operation of making the thickness of the denture base stabilizing sheet uniform is considerably difficult for those who are not accustomed to it. Besides, it often happens that the user has to remove some excess sheet left protruding through the gap between the denture base and the jaw, and some skill is required to avoid such an inconvenient operation. In addition, the denture base stabilizing sheet of a soft sheet type is not desirable from the viewpoint of economy, since a considerable amount thereof is thrown away as excess when forming it into the required size and configuration. Moreover, it is not desirable from the hygienic point of view since the user often touches the denture base stabilizing sheet directly with user's bare hands while forming it.

Trying to solve the problems experienced with the conventional denture base stabilizing sheets, we have developed a shaped article having a particular configuration, and made of denture base stabilizing sheet manufactured using a composition comprising 41 to 43 wt % of ethyl methacrylate polymer, 37 to 39 wt % of butyl phthalyl glycolate, and 17 to 23 wt % of glyceryl triacetate. It was confirmed that the shaped article enables the user to stabilize his or her denture base on the jaw, with ease and in a hygienic manner. The denture base stabilizing sheet of this invention shows an excellent fit, feeling, anti-creep property, satisfactory workability during shaping and satisfactory releasability between the denture base and the denture base stabilizing sheet after use of the denture base.

SUMMARY OF THE INVENTION

In first aspect of this invention, there is provided a denture base stabilizing sheet for stabilizing a denture base on the jaw, comprising a composition containing 41 to 43 wt % of ethyl methacrylate polymer, 37 to 39 wt % of butyl phthalyl butyl glycolate, and 17 to 23 wt % of glyceryl triacetate.

The denture base stabilizing sheet of this invention may further contain a minute amount of titanium oxide.

In second aspect of this invention, there is provided a shaped article made of a denture base stabilizing sheet for stabilizing a denture base on the jaw, comprising a composition containing 41 to 43 wt % of ethyl methacrylate polymer, 37 to 39 wt % of butyl phthalyl butyl glycolate, and 17 to 23 wt % of glyceryl triacetate, having a configuration fitted to the configurations of the jaw and the denture base, and being provided with a punched portion at the center of the sheet.

The denture base stabilizing sheet is formed in an approximate trapezoid which is defined by a front edge, a rear edge, a left side edge and a right side edge, the front and rear edges are parallel to each other, the front edge is shorter than the rear edge, the trapezoid is symmetrical with respect to a central axis which is perpendicular to the rear edge, each corner of the trapezoid is defined by a smooth curve connecting adjacent edges, and the central portion of the rear edge is deformed toward the center of the trapezoid.

DETAILED DESCRIPTION OF THE INVENTION

Figure 1:
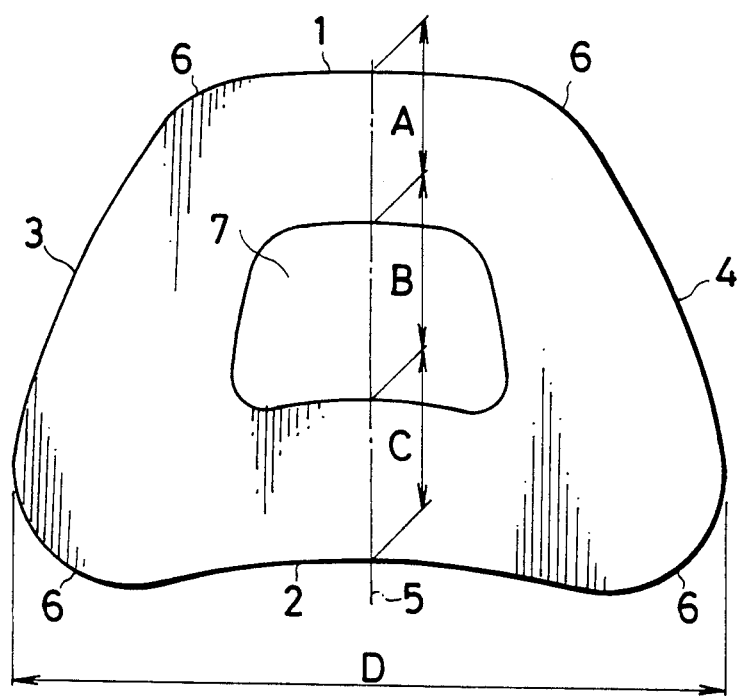
FIG. 1 is a plan view showing a first embodiment of a molded article of a denture base stabilizing sheet for the upper jaw in accordance with this invention.

The denture base stabilizing sheet of this invention may include 41 to 43 wt %, preferably 41.5 to 42.5 wt % of ethyl methacrylate polymer; 37 to 39 wt %, preferably 37 to 38 wt % of butyl phthalyl butyl glycolate; 17 to 23 wt %, preferably 19 to 21.5 wt % of glyceryl triacetate, and a minute amount of additives, if necessary.

The butyl phthalyl butyl glycolate of a boiling point of 210°~220° C. (5 mmHg) [$C_4H_4COOC_4H_4COCH_2COOC_4H_9$] and the glyceryl triacetate of a boiling point of 285° C. used in this invention show a function of plasticizers, and the characteristic of solidifying with the passage of time depending on the temperature and the amount of moisture in the mouth.

Titanium oxide or the like may be added to the composition of this invention. The content of the titanium oxide is preferably 0.01 to 0.3 wt %, more preferably 0.05 to 0.2 wt %.

The ethyl methacrylate polymer used as the shape-formation material for forming the denture base stabilizing sheet in this invention has a number-average molecular weight of 145,000 to 170,000, whereby bringing to the denture base stabilizing sheet the following properties:

1. The sheet is not dissolved into water or saliva.
2. The sheet does not readily induce adhesion of food refuse.
3. The sheet does not feel sticky against the mucous membrane of the mouth, so that it does not involve discomfort in use.
4. The sheet can be washed with cold water or lukewarm water after meals.
5. The sheet does not involve harmful side effects after long use.
6. The sheet adheres to the denture bed without the aid of an adhesive.
7. Hardening takes place gradually.
8. The sheet hardens about 3 days, withstanding long use (about 2 weeks).
9. The sheet hardened can be used as a female die in preparing a new denture base.

It is difficult to attain the object of this invention if the content of the ethyl methacrylate polymer is less than 41 wt % or more than 43 wt %.

If the content of the glyceryl triacetate is less than 17 wt % or the content of the butyl phthalyl butyl glycolate is less than 37 wt %, the denture base stabilizing sheet will cause discomfort to the wearer, and the workability during shaping of the denture base stabilizing sheet and the releasability after use of the denture base will tend to deteriorate. If the content of glyceryl triacetate exceeds 23 wt % or the content of the butyl phthalyl butyl glycolate exceeds 39 wt %, the denture base stabilizing sheet will soften, the workability during the shaping the denture base stabilizer material and the releasability after use of the denture base tending to deteriorate.

The denture base stabilizing sheet of this invention has viscosities (torques) of 4.00 to 5.00 kg-cm at 23° C. and 2.50 to 3.50 kg-cm at 37° C., preferably 4.30 to 4.70 kg-cm at 23° C. and 2.80 to 3.20 kg-cm at 37° C.

The viscosity (torque) of the denture base stabilizing sheet is measured under the atmosphere of (i) 23°±1° C. and 50±5% RH, and (ii) 37°±1° C. and 50±5% RH by using JSR Curust Meter (manufactured by Imanaka Kikai Kogyo Kabushiki Kaisha, UMT-580), in which a dies for use in rubber is employed, the thickness of the speciment is 3 mm and the oscilating angle is 3°.

It is desirable that the denture base stabilizing sheet of this invention is shaped into a particular configuration. Examples of such a configuration will now be described with reference to the embodiments shown in the attached drawings.

FIG. 1 shows one embodiment of a molded article of a denture base stabilizing sheet for the upper jaw.

The shaped article of denture base stabilizing sheet shown in FIG. 1 has an approximately trapezoidal configuration defined by a front edge 1, a rear edge 2, a left side edge 3 and a right side edge 4. The front edge 1 and the rear edge 2 are parallel to each other, the front edge 1 being shorter than the rear edge 2. This trapezoid is symmetrical with respect to a central axis 5 which is perpendicular to the rear edge 2. The front edge 1, the left side edge 3 and the right side edge 4 form approximately straight lines which are slightly curved, each corner 6 of the trapezoid being defined by a curve having a certain curvature. The rear edge 2 is slightly deformed toward the center of the trapezoid and is defined by a curve having a certain curvature. Provided at the center of this trapezoid is a punched portion 7 having an approximately trapezoidal configuration similar to that of the outer trapezoid and equipped with a front edge, a rear edge, a left side edge and a right side edge, each of which is reduced in its size similarly to the corresponding edge of the outer trapezoid.

Provision of the punched portion 7 brings about the following advantages. When pressing the denture base together with a denture base stabilizing sheet against the jaw after attaching to the jaw the denture base fixing the denture base stabilizing sheet, a portion of the upper jaw contacting with the denture base stabilizing sheet dents but a portion of the upper jaw opposing to the punched portion 7 does not dent. Accordingly, the space volume deffined by the punched portion 7 decreases, so that air trapped in the punched portion 7 is forced out in the side directions through gaps between the upper jaw and the denture base stabilizing sheet when clenching. After that, on stopping to press the denture base toward the upper jaw, the dent of the upper jaw is restored to the former state, whereby negative pressure is generated in the space defined by the punched portion, and the denture base is sucked toward the jaw to be firmly retained on the jaw. Further, due to the punched portion 7, the portion of the jaw corresponding to the punched portion 7 is not pressed by the denture base stabilizing sheet and thus the mucous membrane, the blood vessels and the nerves under the denture base are protected.

In addition, this shaped article of denture base stabilizing sheet may be made of a mesh-like plate. In this case, the force for retaining the denture base on the jaw can be further increased, and the amount of the denture base stabilizing sheet can be reduced.

The configurations of each corner 6 and the deformation of the rear edge 2 toward the trapezoid center are not restricted to curves having a certain curvature. Any other curved lines may be adopted for them.

In an embodiment, the size of each section is as follows:

Distance A between the front edge 1 of the shaped article and that of the punched section 7 as measured along the center line 5: about 20 mm;

Distance B between the front edge and rear edge of the punched portion 7 as measured along the center line 5: about 25 mm;

Distance C between the rear edge of the shaped article and that of the punched portion 7 as measured along the center line 5: about 20 mm; and Maximum width D of the rear edge portion: about 100 mm.

Figure 2:
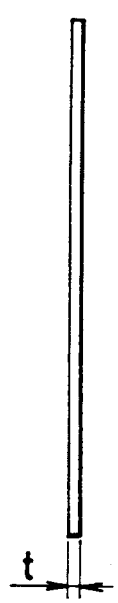
FIG. 2 is a side view of the molded article of the denture base stabilizing sheet shown in FIG. 1.

FIG. 2 is a side view of the sheet shown in FIG. 1, indicating a uniform plate thickness of the shaped article.

The plate thickness t in one embodiment is 1 to 5 mm.

Figure 3:
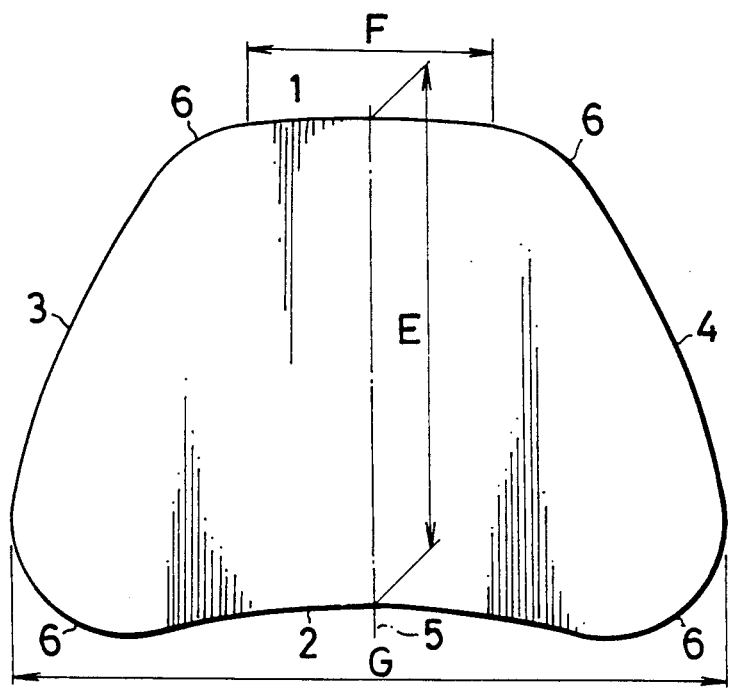
FIGS. 3 and 4 are plan views showing a second embodiment and a third embodiment, respectively, of a molded article of a denture base stabilizing sheet for the upper jaw in accordance with this invention.

FIG. 3 shows another embodiment of the molded article of denture base stabilizing sheet for the upper jaw, in which the molded article has fundamentally the same configuration as that of the shaped article shown in FIG. 1, but differs from the latter in that no punched portion 7 is disposed at the center. Thus, the shaped article of denture base stabilizing sheet may be formed without any punched portion.

In the embodiment shown in FIG. 3, the size of each section is as follows:

Height E of the trapezoid as measured along the center line 5: about 68 mm;

Length F of the approximately linear section of the front edge 1: about 40 mm;

Maximum width G of the rear edge section: about 100 mm; and

Plate thickness t: about 1 to 5 mm.

Figure 4:
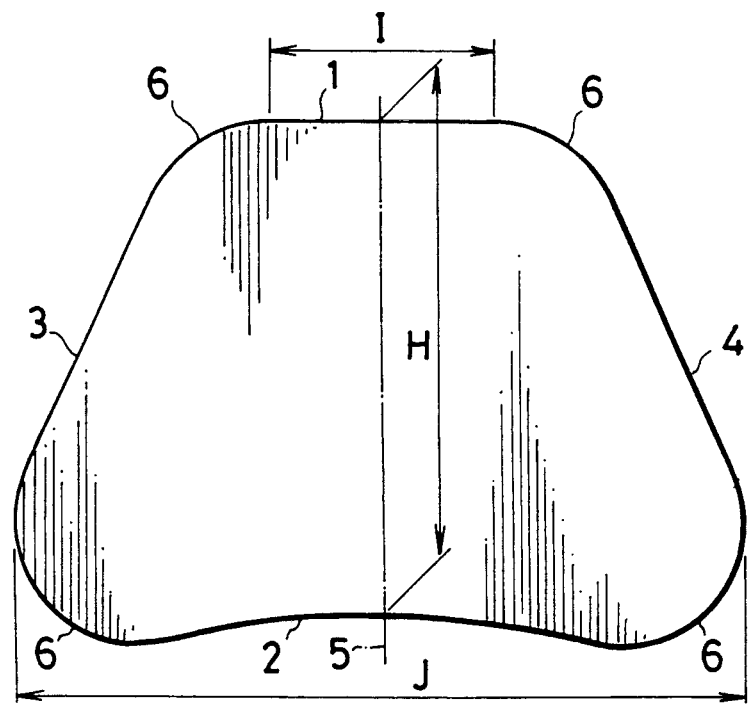

FIG. 4 shows still another embodiment of the shaped article of denture base stabilizing sheet for the upper jaw, in which the shaped article has fundamentally the same configuration as that of the shaped article shown in FIG. 3, but differs from the latter in that its front edge 1, left side edge 3 and right side edge 4 are straight lines.

In the embodiment shown in FIG. 4, the size of each section is as follows:

Height H of the trapezoid as measured along the center line 5: about 66 mm;

Length I of the linear section of the front edge 1: about 40 mm;

Maximum width J of the rear edge section: about 99 mm; and

Plate thickness t: 1 to 5 mm.

Figure 5:
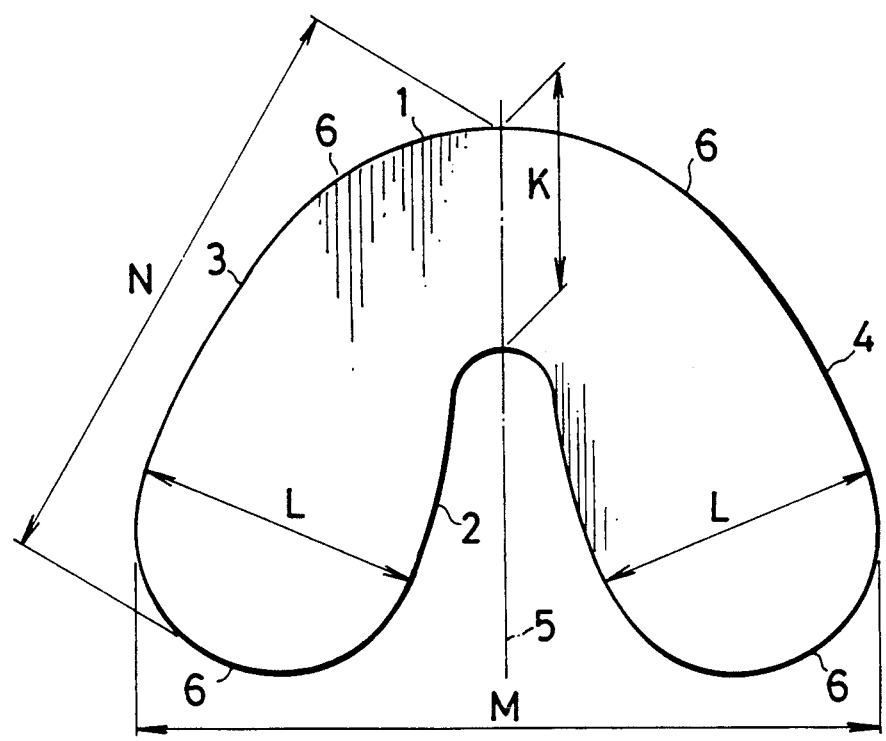
FIGS. 5 and 6 are plan views showing a first embodiment and a second embodiment, respectively, of a molded article of a denture base stabilizing sheet for the lower jaw in accordance with this invention.

FIG. 5 shows one embodiment of the shaped article of denture base stabilizing sheet for the lower jaw.

The shaped article shown in FIG. 5 has an approximately trapezoidal configuration which is defined by a front edge 1, a rear edge 2, a left side edge 3 and a right side edge 4. The front edge 1 and rear edges 2 are parallel to each other, the front edge 1 being shorter than the rear edge 2. This trapezoid is symmetrical with respect to a central line 5 which is perpendicular to the rear edge 2. The left edge 3 and right side edge 4 form approximately straight lines which are slightly curved.

Further, this trapezoid is devoid of any linear section in the front edge 1 because of the large curvatures of the corners adjacent to the front edge 1. The curves of the corners adjacent to the rear edge 2 constitute semicircles, and rear edge 2 is deformed toward the central portion of the trapezoid so that a central section of the rear edge 2 defines a semicircle. This deformation of the rear edge 2 toward the trapezoid center helps to avoid interference between the tongue and the shaped article of denture base stabilizing sheet. In addition, this shaped article may be made of a mesh-like plate material. In this case, the force for retaining the denture base on the jaw can be further increased. In the embodiment shown in FIG. 5, the configurations of each corner and the deformation of the rear edge 2 toward the trapezoid center are not restricted to semicircles and a curve having a certain curvature, respectively. Any other curved line may be adopted.

In the embodiment shown in FIG. 5, the size of each section is as follows:

Distance K between the front edge and the rear edge deformed toward the trapezoid center as measured along the center line: about 30 mm;

Diameter L of the semicircles defining the corners adjacent to the rear edge 2: about 38$\phi$ mm;

Maximum width M of the rear edge section: about 100 mm;

Distance N between the center of the front edge 1 and the respective corners adjacent to the rear edges: about 82 mm; and Plate thickness t: 1 to 5 mm.

In this embodiment, N may be a value other than 82 mm.

Figure 6:
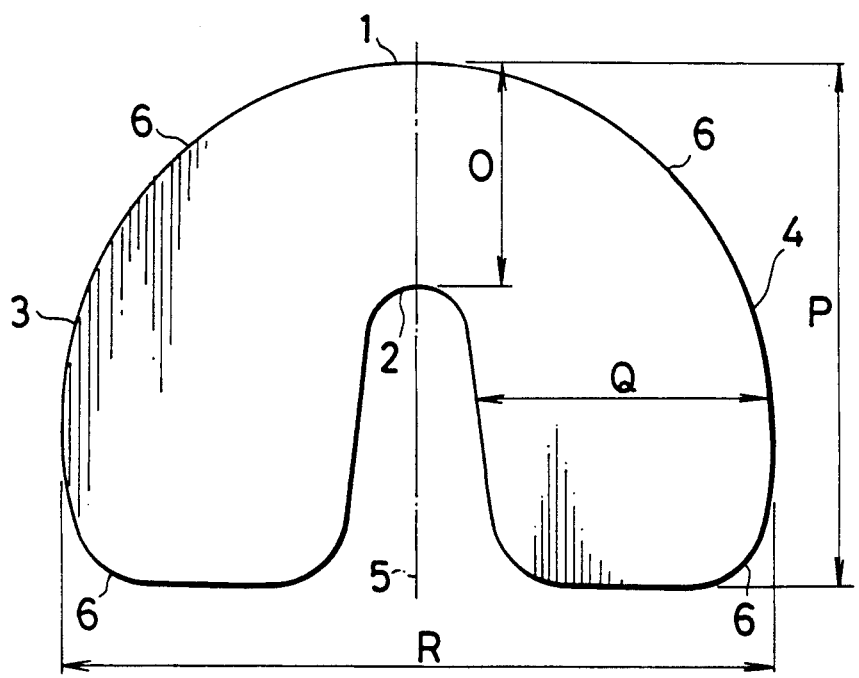

FIG. 6 shows another embodiment of the shaped article of denture base stabilizing sheet for the lower jaw. The shaped article shown in FIG. 6 has the same fundamental configuration as that of the shaped article shown in FIG. 5, but differs from the latter in that its left side edge 3 and right side edge 4 are perpendicular to its rear edge 2. The configurations of each corner and the deformation of the rear edge toward the trapezoid center are not restricted to semicircles and a curve having a certain curvature. Any other curved line may be adopted.

In this embodiment, the size of each section is as follows:

Distance 0 between the front edge 1 and the rear edge 2 deformed toward the trapezoid center as measured along the center line 5: about 30 mm;

Maximum height P of the trapezoid: about 70 mm;

Distance Q between the respective side edges 3, 4 and the deformed section of the rear edge 2 recessed toward the trapezoid center: about 40 mm;

Maximum width R of the rear edge section: about 97 mm; and

Plate thickness t: 1 to 5 mm.

The shaped article of denture base stabilizing sheet of this invention, having a particular configuration can be produced by well known methods. For example, a synthetic resin composition including ingredients in a predetermined proportion is kneaded well, thus kneaded composition is then spread into a sheet or a mesh-like plate having a predetermined thickness, and thus produced material is punched into a desired configuration. Alternatively, the kneaded composition can be molded into a desired configuration by the use of a female mold.

The thickness of the shaped article of denture base stabilizing sheet of this invention is 0.2 to 5 mm, preferably 0.5 to 3 mm, and more preferably 0.8 to 1.5 mm.

The shaped article of denture base stabilizing sheet of this invention may be used in the following manner. First, the shaped article denture base stabilizing sheet in the state of a soft plate is stuck to a denture base, which is inserted into the mouth. After attaching the molded article to the jaw, the denture base is pressed against the jaw by clenching the teeth. Since the shaped article of denture base stabilizing sheet before hardening is soft, it is deformed by this pressurizing force, resulting in filling up any gap left between the denture base and the jaw and in stabilizing the denture base on the jaw. Because of its hardening characteristics, the shaped article of denture base stabilizing sheet hardens with the passage of time depending on the temperature and the amount of moisture in the mouth.

In accordance with this invention, denture base stabilizing sheet composition is composed of 41 to 43 wt % of ethyl methacrylate polymer, 37 to 39 wt % of butyl phthalyl butyl glycolate, and 17 to 23 wt % of glyceryl triacetate. Because of this composition, the denture base stabilizing sheet can be hardened by the body temperature and the saliva upon being positioned on the jaw (excellence in retardation property in hardening), allowing the denture base to be stabilized on the jaw with ease (excellence in form stability). Furthermore, it provides comfortable feeling for the wearer of the denture base (excellence in adhesion properties to the denture base), exhibits a satisfactory workability while it is being formed into a particular configuration and shows a satisfactory releasability between the denture base and the shaped article of denture base stabilizing composition after use of the denture base.

On the other hand, since the shaped article of denture base stabilizing sheet is shaped beforehand into a configuration conforming to the configurations of the jaw and the denture base, the user is released, each time the user attaches his or her denture base to his or her jaw, from the bothersome operation of taking the required amount of denture base stabilizing material in the form of powder or paste out of a receptacle and of disposing it on the denture base, or of forming the material into a soft plate conforming to the size and configuration of the denture base, or from the difficult operation of making the thickness of the denture base stabilizing material uniform, thereby making it possible for anyone to attach his or her denture base to user's jaw and to stabilize it on user's jaw with ease and in a reliable manner, without exhausting user's nerves.

In addition, the shaped article of denture base stabilizing sheet of this invention is relatively economical since it involves less amount of excess material than unformed soft denture base stabilizing materials which has to be shaped into a desired form by the user. Furthermore, it is hygienic since the user does not have to touch the molded article so often during attaching operation.

This invention will now be described more specifically with reference to examples thereof, which should not be construed as restrictive.

EXAMPLE AND COMPARISON EXAMPLE 7240 g of ethyl methacrylate polymer having a number-average molecular weight of 154,000, 6464 g of butyl-phthalyl butyl glycolate (Trade name: MOR-FLEX 190) having $d_4^{20}$ of 1.104±0.002 and a boiling point of 210° to 220° C. (5 mmHg), 3516 g of glyceryl triacetate (Trade name: TRIACETIN) having $d_4^{20}$ of 1.163 and a boiling point of 285° C., and 17 g of titanium oxide were mixed. The thus obtained mixture was sufficiently kneaded and the kneaded composition was subjected to heat-press treatment, thereby obtaining sheet having a thickness of 1 mm. The sheet was punched into a desired configuration, thereby obtaining shaped article of denture base stabilizing sheet having the configuration which is shown in FIG. 3 and having a composition shown in Table 1.

Further, the denture base stabilizing sheet having a composition shown in Table 1 and a thickness of 3 mm showed viscosities (torques) of 4.45 kg-cm (23°±1° C.) and 2.94 kg-cm (37°±1° C.).

The shaped article of denture has stabilizing sheet having a composition shown in Table 1 as the Comparative Example was prepared by the same method.

Using the shaped articles thus obtained, the following tests were conducted:

1) Fit-feeling properties

The fit-feeling of the shaped articles of denture base stabilizing sheet was judged by 30 panelists during 2 weeks.
Evaluation was made using the following criteria:
A . . . Found comfortable by 25 persons or more.
B . . . Found comfortable by 11 to 24 persons.
C . . . Found comfortable by 1 to 10 persons.

2) Releasability

The releasability of the shaped articles of denture base stabilizing sheet from the denture base after 2 weeks of continuous use was judged by the same 30 panelists.
Evaluation was made using the following criteria.
A . . . Judged the shaped article to be releasable with fingers of 28 persons or more.
B . . . Judged the shaped article to be releasable with fingers of 15 to 27 persons.
C . . . Judged the shaped article to be releasable with fingers of 1 to 14 persons.

3) Adhesive properties

The adhesive properties of the shaped articles of denture base stabilizing sheet to the denture base during 2 weeks of continuous use were judged by the same 30 panelists.
Evaluation was made using the following criteria:
A . . . No peeling off with 23 persons or more.
B . . . No peeling off with 11 to 22 persons.
C . . . No peeling off with 1 to 10 persons.

4) Workability

The workability of the shaped articles of denture base stabilizing sheet during fitting the shaped article to the denture base was judged by five dentists.
Evaluation was made using the following criteria:
A . . . Excellent
B . . . Ordinary
C . . . Poor 5) Retardation property in hardening The retardation property in hardening with respect to the shaped article of denture base stabilizing sheet was judged after attaching it to denture base (at 37° C. and in the presence of saliva).

The hardening time of 3 to 4 days is more desiable. If the hardening time is within 1 day, the fit-feeling properties, the adhesive properties and the workability deteriorate, and if the hardening time is more than 7 days, the fit-feeling properties, the adhesive properties and form-stability (anti-creep characteristics) deteriorate.
Evaluation was made using the following criteria:
A . . . 3 to 4 days were necessary for hardening.
B . . . 1 to 2 days or 5 to 7 days were necessary for hardening completely.
C . . . Hardened within 1 days, or more than 7 days were necessary for hardening.

6) Form-stability (anti-creep characteristics)

The changes in configuration of the shaped article of denture base stabilizing sheet after being placed in the jaws of the above-mentioned 30 panelists were observed for 2 weeks.
Evaluation was made using the following criteria:
A . . . Some changes in configuration were observed with less than 5 persons.
B . . . Some changes in configuration were observed with 5 to 15 persons.
C . . . Some changes in configuration were observed with less than 15 persons.

The results of evaluation are shown in Table 2.

TABLE 1

| Material | Proportion (wt %) | |
|---|---|---|
| | Example | Comp. Ex. |
| Ethyl methacrylate polymer | 42.0 | 39.8 |
| Butyl phthalyl butyl glycolate | 37.5 | 36.0 |
| Glyceryl triacetate | 20.4 | 24.2 |
| Titanium oxide | 0.1 | |

TABLE 2

| Material | Example | Comp. Ex. |
| --- | --- | --- |
| Fit-feeling | A | B |
| Releasability | A | A |
| Adhesion properties | A | B |
| Workability | A | A |
| Retardation property in hardening | A | C |
| Form-stability | A | C |

$LD_{50}$ (saline extract) of the denture base stabilizing sheet of Example is more than 20 ml/kg and as a result the denture base stabilizing sheet of the present invention are classified as non-toxic in rats.

A denture base stabilizing sheet which can be put into practical use must exhibit a standard of A in all of these items: feeling during wear, releasability, adhesion properties, workability, retardation property in hardening and form stability.

What is claimed is:

1. A denture base stabilizing sheet for stabilizing a denture base on the jaw, comprising a composition consisting essentially of 41 to 43 wt % of ethyl methacrylate polymer, 37 to 39 wt % of butyl phthalyl butyl glycolate, and 17 to 23 wt % of glyceryl triacetate.

2. A denture base stabilizing sheet according to claim 1, consisting essentially of about 41.5 to 42.5 wt % of ethyl methacrylate polymer, about 37 to 38 wt % of butyl phthalyl butyl glycolate and 19 to 21.5 wt % of glyceryl triacetate.

3. A denture base stabilizing sheet according to claim 2, which further contains 0.01 to 0.3 wt % titanium dioxide.

4. A denture base stabilizing sheet according to claim 1, which further contains 0.01 to 0.3 wt % titanium dioxide.

5. A denture base stabilizing sheet for stabilizing a denture base on the jaw, which comprises a composition consisting essentially of 41 to 43 wt % of ethyl methacrylate polymer, 37 to 39 wt % of butyl phthalyl butyl glycolate, and 17 to 23 wt % of glyceryl triacetate, and which has a configuration substantially of a trapezoid which has a front edge, a rear edge, a left side edge and a right side edge, said front edge being shorter than said rear edge, said trapezoid being symmetrical with respect to the central axis thereof which is perpendicular to said rear edge, each corner of said trapezoid being defined by a smooth curve connecting adjacent edges, and a central portion of said rear edge being slightly deformed toward a center of said trapezoid.

6. A denture base stabilizing sheet according to claim 5, which further contains 0.01 to 0.3 wt % titanium dioxide.

7. A denture base stabilizing sheet for stabilizing a denture base on the jaw, which comprises a composition consisting essentially of 41 to 43 wt % of ethyl methacrylate polymer, 37 to 39 wt % of butyl phthalyl butyl glycolate and 17 to 23 wt % of glyceryl triacetate, and which has a configuration substantially of a trapezoid which has a front edge, a rear edge, a left side edge and a right side edge, said front edge and said rear edge being parallel to each other, said front edge being shorter than said rear edge, said trapezoid being symmetrical with respect to the central axis thereof which is a perpendicular to said rear edge, each corner of said trapezoid being defined by a smooth curve connecting adjacent edges, and the central portion of said rear edge being deformed adjacent the center of said trapezoid.

8. A denture base stabilizing sheet according to claim 7, which further contains 0.01 to 0.3 wt % titanium dioxide.

* * * * *